United States Patent [19]
Okazaki et al.

[11] Patent Number: 5,810,997
[45] Date of Patent: Sep. 22, 1998

[54] AIR-FUEL RATIO DETECTION WITH VARIABLE DETECTION RANGE

[75] Inventors: Kazuhiro Okazaki, Anjo; Tomomichi Mizoguchi, Nagoya, both of Japan

[73] Assignee: Nippondenso Co., Ltd., Kariya, Japan

[21] Appl. No.: 688,263

[22] Filed: Jul. 29, 1996

[30] Foreign Application Priority Data

Aug. 30, 1995 [JP] Japan .................................. 7-221323

[51] Int. Cl.⁶ .................................................. G01N 27/407
[52] U.S. Cl. ........................................ 205/784.5; 204/425
[58] Field of Search .................................. 204/421–429; 205/783.5, 784, 784.5

[56] References Cited

U.S. PATENT DOCUMENTS

| | | |
|---|---|---|
| 4,472,247 | 9/1984 | Rohr et al. ............................ 204/425 |
| 4,601,793 | 7/1986 | Asayama et al. . |
| 4,626,338 | 12/1986 | Kondo et al. . |
| 4,759,827 | 7/1988 | Okada et al. ......................... 204/425 |

FOREIGN PATENT DOCUMENTS 6-137193  5/1994  Japan .
7-50070   5/1995  Japan .

*Primary Examiner*—T. Tung
*Attorney, Agent, or Firm*—Nixon & Vanderhye P.C.

[57] ABSTRACT

In an air-fuel ratio control of an engine, an oxygen sensor element is operated with an operating voltage for producing an electric current corresponding to an air-fuel ratio of mixture. The operating voltage is varied in accordance with a range of the air-fuel ratio to be detected, i.e., lean air-fuel ratio, stoichiometric air-fuel ratio or rich air-fuel ratio. The operating voltage may be varied in correspondence to the actual electric current produced from the sensing element or a target value of the air-fuel ratio to which the engine is feedback-controlled.

14 Claims, 6 Drawing Sheets

FIG. 4

| CONTROL MODE | POWER SUPPLY VOLTAGE | | A/D INPUT VOLTAGE | | CURRENT DETECTION | | REF. VOLT. | RESISTANCE | | | SWITCH 24, 25 |
|---|---|---|---|---|---|---|---|---|---|---|---|
| | V− | V+ | min. | max. | RANGE | WIDTH | | | | | |
| LEAN | −12 | 12 | 0V | 5V | −2.5~15mA | 12.5mA | −1V | R10=400Ω | R11=11.8KΩ | R12=10KΩ | A |
| STOICHIOMETRIC | −12 | 12 | 0V | 5V | −5~5mA | 10mA | 2.5V | R20=500Ω | R21=6.55KΩ | R22=10KΩ | B |
| RICH | −12 | 12 | 0V | 5V | −15~2.5mA | 12.5mA | 6V | R30=400Ω | R31=3.33KΩ | R32=10KΩ | C |

AIR-FUEL RATIO DETECTION WITH VARIABLE DETECTION RANGE

BACKGROUND OF THE INVENTION

1. Field of the Invention

The present invention relates to an air-fuel ratio detecting apparatus and method which is used for detecting oxygen concentration or other combustible gas (CO, HC, $H_2$) concentration in gases such as an engine exhaust gas.

2. Description of Related Art

It is well known in the art to effect feedback control, by use of an oxygen sensor, of the air-fuel ratio of an air-fuel mixture supplied to an internal combustion engine e.g., to meet exhaust gas regulations and/or requirements for a reduction in fuel consumption.

For such an oxygen sensor, a pumping current type or limiting current type which uses an oxygen ion conductive solid electrolyte is used as exemplified in JP-B2 7-50070. With this oxygen sensor, a rich or lean air-fuel ratio (fuel-rich condition or fuel-lean condition) is detected based on the flow direction of electric pumping current of the oxygen sensor. A gain factor is then switched based on the detected current flow directions so that the oxygen sensor produces an electric output current varying in proportion to the concentration of oxygen or other combustible gas concentration in the gas. However, the air-fuel ratio detection range of such an oxygen sensor is limited, while the detectable range of air-fuel ratio is desired to be much wider.

SUMMARY OF THE INVENTION

It is, therefore, an object of the present invention to provide an air-fuel ratio detecting apparatus and method which is capable of detecting an air-fuel ratio in a much wider detection range.

It is a further object of the invention to provide such an air-fuel ratio detecting apparatus and method without necessitating complication in construction nor increase in production cost.

According to the present invention, an oxygen responsive sensor element is supplied with an operating voltage to produce an electric output current which varies with oxygen concentration. The operating voltage is switched to shift the air-fuel ratio detection range in accordance with the electric output current from the sensor element. Alternatively, in the case of air-fuel ratio feedback control, the operating voltage may be switched in accordance with a target air-fuel ratio which is set for the feedback control.

Preferably, a current detecting circuit is connected to the sensor element and includes a plurality of resistors for current-voltage conversion. The resistors used for the current-voltage conversion are switched in accordance with the air-fuel ratio detection range.

More preferably, the resistors of the current detecting circuit are grouped for detecting the air-fuel ratio in a wide range and for detecting the air-fuel ratio at a specified range within the wide range.

BRIEF DESCRIPTION OF THE DRAWINGS

Other objects, features and advantages of the present invention will become more apparent from the following description made in conjunction with the accompanying drawings, in which:

FIG. 4 is a table illustrating details of circuit construction of the embodiment of FIG. 1;

DETAILED DESCRIPTION OF THE PRESENTLY PREFERRED EMBODIMENTS

The present invention will be described in more detail with reference to the accompanying drawings.

Figure 1:
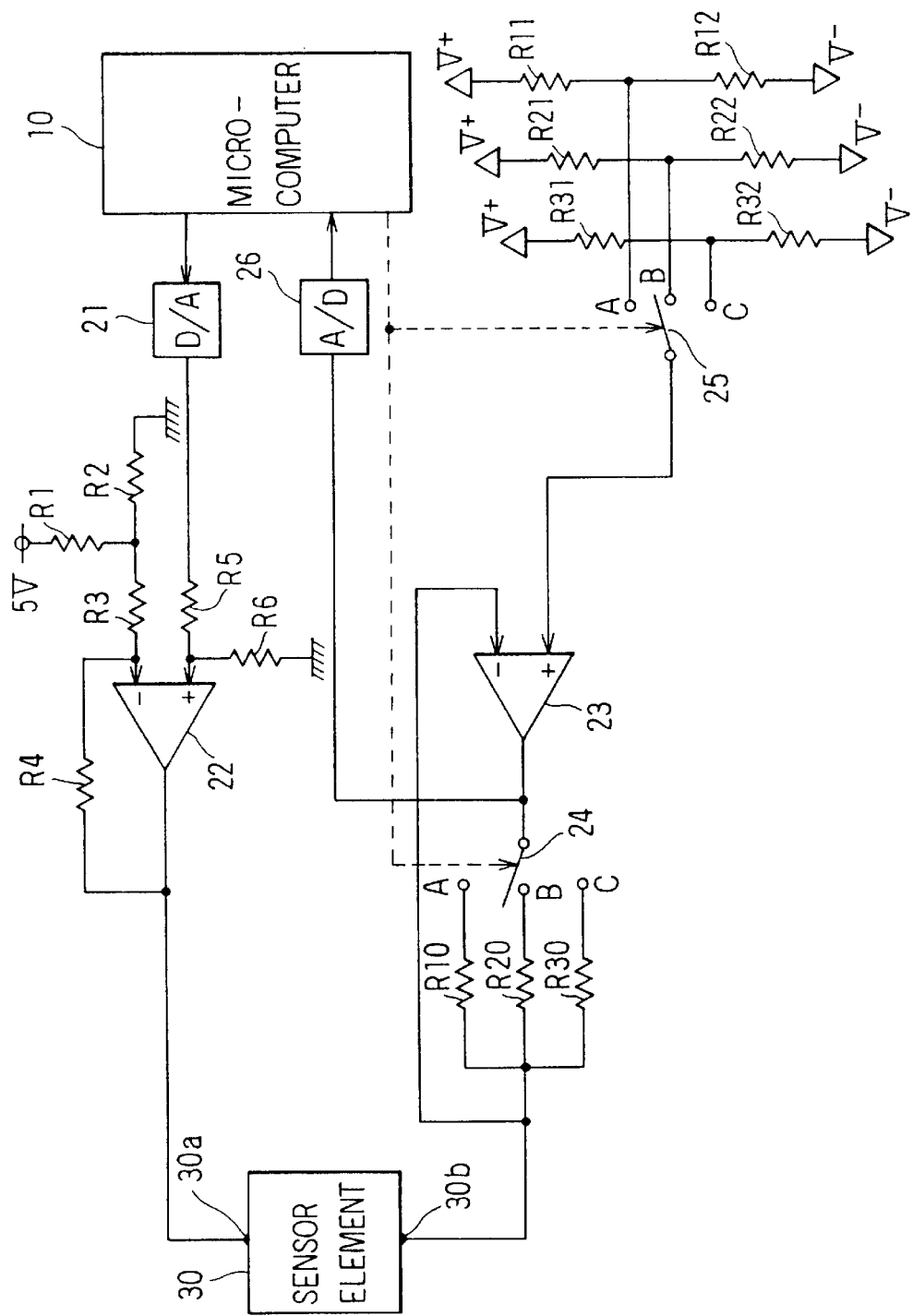
FIG. 1 is an electric wiring diagram illustrating an air-fuel ratio detecting apparatus according to an embodiment of the present invention.

In an embodiment illustrated in FIG. 1, an oxygen responsive sensor element 30 uses an oxygen ion conductive solid electrolyte and mounted on an exhaust system of an engine (not illustrated) in which the air-fuel ratio of its input air-fuel mixture is feedback controlled to a target air-fuel ratio in response to the oxygen concentration detected in the exhaust system. The sensor element 30 is connected to be controlled by a microcomputer 10, which includes a CPU, ROM, RAM, input/output circuit and the like, through a digital-analog (D/A) converter circuit 21 and an operational amplifier 22 with resistors R1 through R6. The microcomputer 10 is programmed to control the converter circuit 21 to provide the amplifier 22, i.e., the noninverting input terminal (+), with a voltage (0V to 5V) which is divided by the resistors R5 (10 KΩ) and R6 (40 KΩ). The amplifier 22 receives at its inverting input terminal (−) a power supply voltage (5V) through the resistors R1 to R3 (all 10 KΩ). The amplifier 22 has the resistor R4 (10 KΩ) for negative feedback. The sensor element 30 is connected to the output terminal of the amplifier 22 at one terminal 30a thereof to receive a voltage of −10V to 10V from the amplifier 22. Thus, the voltage to the terminal 30a is varied in accordance with the target air-fuel ratio of the feedback control.

The sensor element 30 is further connected at the other terminal 30b thereof to the inverting input terminal (−) of an operational amplifier 23, and also to resistors R10 to R30 which is selectively connectable to the output terminal of the amplifier 23 through a change-over switch 24. The resistors R10 to R30 are used to detect electric currents of the sensor element 30. Power supply voltages in positive and negative polarities V+ (12 V) and V− (−12 V) are divided by resistors R11 and R12, R21 and R22, and R31 and R32 to be selectively applied to a noninverting input terminal (+) of the amplifier 23 through a change-over switch 25. The two switches 24 and 25 are so controlled by the microcomputer 10 to contact the same terminals A, B and C of the two resistor networks (R10 to R30, and R11 to R32). With this circuit construction, the sensor element 30 is supplied at the terminal 30b with either one of −1 V, 2.5 V and 6 V as a reference voltage by the change-over operations of the switches 24 and 25.

It is assumed that the microcomputer 10 controls the switches 24 and 25 to contact the terminals B to apply 2.5 V to the terminal 30b of the sensor element 30 as the reference voltage and further controls the converter circuit 21 to apply 2.9 V from the amplifier 22 to the terminal 30a of the sensor element 30. Under this condition, with an operating voltage of 0.4 V (2.9 V–2.5 V) being supplied across the sensor element 30, the sensor element 30 produces from the terminal 30b an electric output current corresponding to both the operating voltage of 0.4 V and the oxygen concentration in the engine exhaust system, i.e., in an response to actual air-fuel ratio of mixture supplied to the engine. The output current from the sensor element 30 at this time is converted into a voltage by the resistor R20 to be applied to the microcomputer 10 through an analog-digital (A/D) converter circuit 26. Thus, the microcomputer 10 in turn detects the results of the present actual air-fuel ratio from the digital value of the voltage across the resistor R20 which is proportional to the output current of the sensor element 30.

In the engine, the air-fuel ratio of input air-fuel mixture should be controlled over a wide range from the fuel-lean side to the fuel-rich side in order to meet various requirements such as reduction in fuel consumption and the least harmful exhaust emissions. This necessitates shifting of the target air-fuel ratio in the feedback control system, i.e., feedback control mode. In order to detect the air-fuel ratio over a wide range by the use of the same sensor element 30, the microcomputer 10 is programmed to vary or shift the detection range of the sensor element output current, i.e., actual air-fuel ratio, based on the air-fuel ratio control modes, in such a manner as illustrated in FIGS. 2 and 3.

Figure 2:
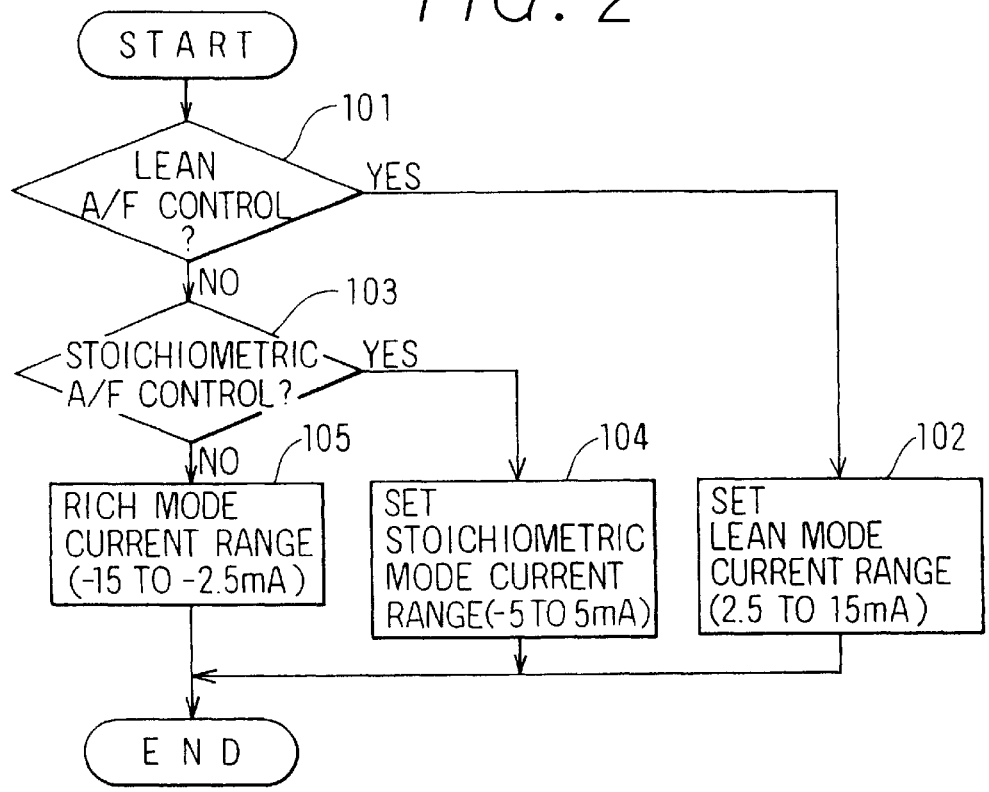
FIG. 2 is a flow chart illustrating a current detection range setting process of a microcomputer performed based on air-fuel ratio control modes.

In FIG. 2, it is first determined at step 101 whether the feedback control mode is in the lean control mode in which the target air-fuel ratio is set to a lean air-fuel ratio for the reduction in fuel consumption. With the determination of YES, the current detection range for the lean control mode is set to 2.5 to 15 mA at step 102 as illustrated in FIGS. 2 and 3. If the control mode is not in the lean mode (NO at step 101), it is further determined at step 103 whether the feedback control mode is in the normal control mode in which the target air-fuel ratio is set to the stoichiometric air-fuel ratio for the reduction in noxious exhaust emissions. With the determination of YES at step 103, the current detection range for the normal stoichiometric control mode is set to –5 to 5 mA at step 104 as illustrated in FIGS. 2 and 3. If the control mode is not in the stoichiometric control mode (NO at step 103), it is considered the rich control mode in which the target air-fuel ratio is set to the rich air-fuel ratio for high engine load operations as well as the reduction in the noxious exhaust emissions, and the current detection range therefor is set to –15 to –2.5 mA at step 105 as illustrated in FIGS. 2 and 3.

In practice of this embodiment, shown in the table in FIG. 4 are the power supply voltages V+ and V–, minimum and maximum input voltages to the analog-digital converter circuit 26, current detection ranges and widths, reference voltages to the sensor element 30a, resistances of the resistors R10 to R32, and positions of switches 24 and 25, for each air-fuel ratio control mode. Thus, by setting the three current detection ranges in correspondence to the three control modes (lean, stoichiometric, rich) as explained above, the output currents of the sensor element 30a can be detected over the wide range of air-fuel ratios with high accuracy. That is, since the minimum and maximum input voltages to the analogdigital converter circuit 26 are determined to change in the same range (0 to 5 V) as shown in FIG. 4, the analog-digital converter 26 need not be of more than 16-bit type but may be of about 10-bit type.

Figure 3:
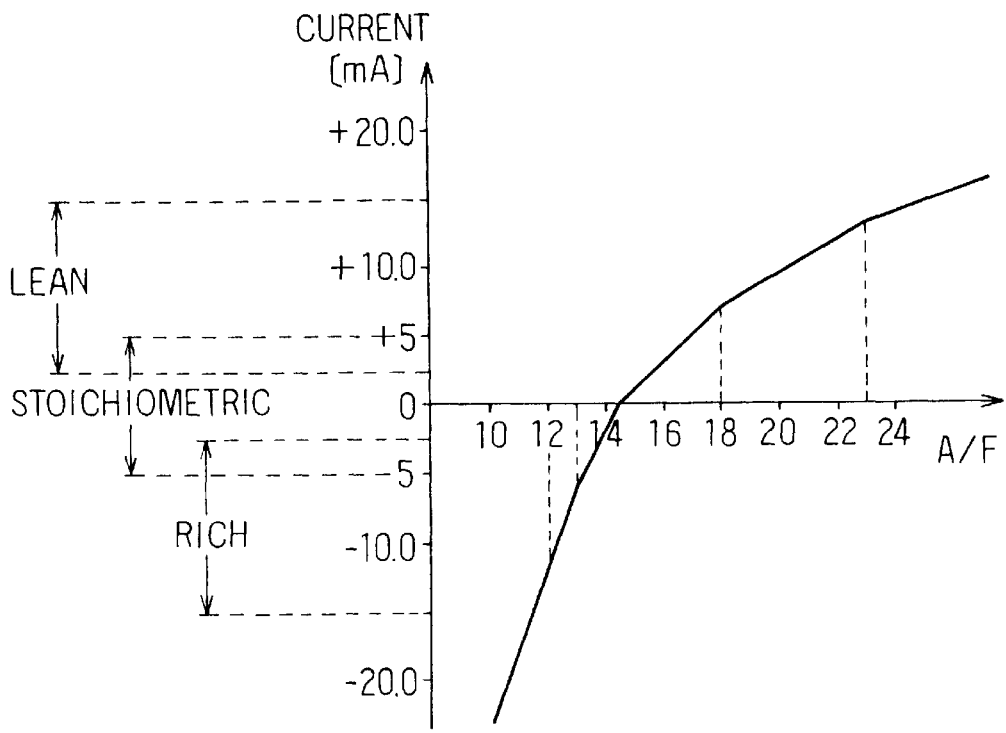
FIG. 3 is a graph illustrating a relation between an air-fuel ratio and a current detection range in each air-fuel ratio control mode.

As illustrated in FIGS. 2 and 3, the microcomputer 10 determines the control modes and changes over the current detection ranges in correspondence to the target air-fuel ratios of the air-fuel ratio feedback control. It may occur that the output current of the sensor element 30a deviates to more than or less than the set detection range due to changes in the engine operating conditions. To counter this, the microcomputer 10 is further programmed to modify the current detection ranges by the process illustrated in FIG. 5.

Figure 5:
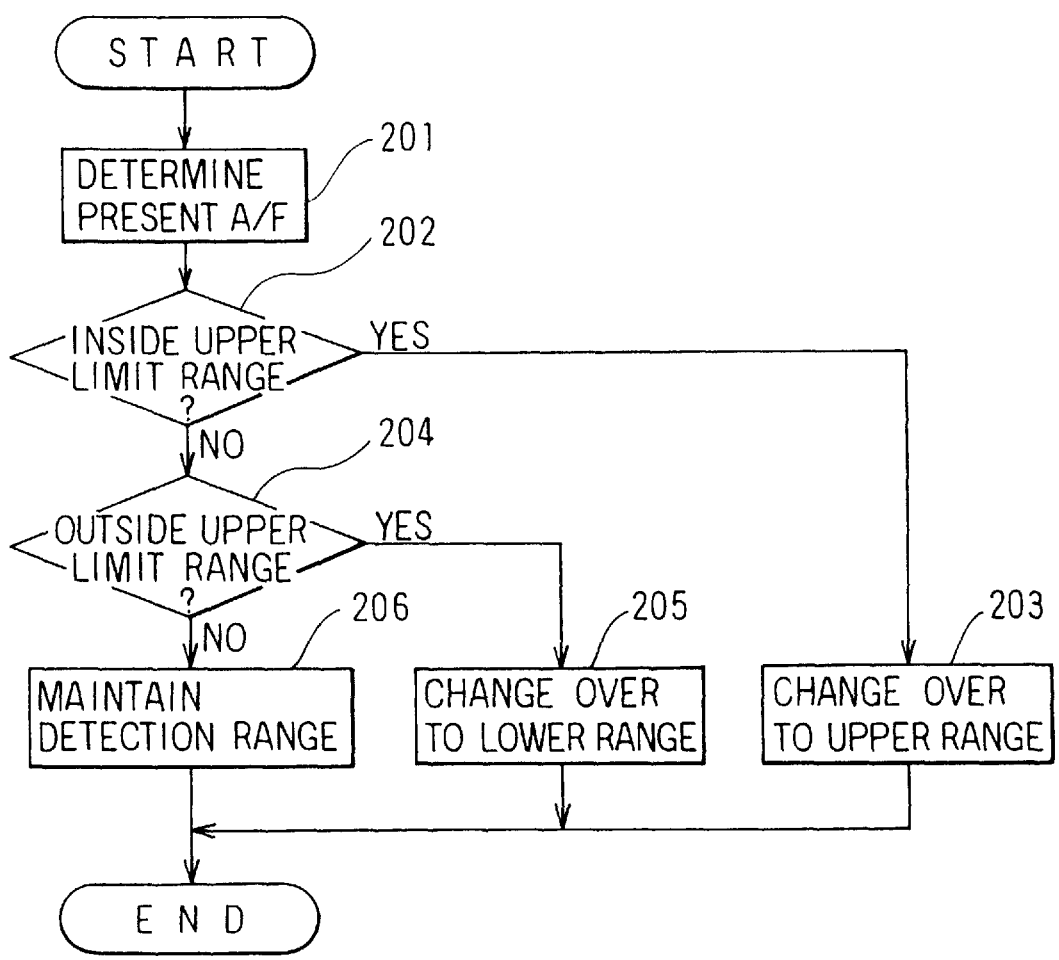
FIG. 5 is a flow chart illustrating a current detection range switching process of the microcomputer.

In FIG. 5, the present actual air-fuel ratio is first determined at step 201 from the detected value of the output current. Then, at step 202, it is determined whether the detected current value resides inside an upper limit range of the presently set current detection range. The upper limit range is set to be about upper 10% of the present current detection range, i.e., within an overlapping range of 20 to 25% between two adjacent current detection ranges of FIG. 3. With the determination of YES at step 202, the presently set current detection range is changed over to the upper one at step 203. For instance, at the time the presently detected current reaches or rises above 4 mA entering the 10% upper limit in the range for the stoichiometric control mode, the detection range is changed over to the upper current detection range of the adjacent control mode, i.e., the lean control mode. In the same manner, the detection range is changed over from the rich control mode to that for the stoichiometric control mode if the presently detected current reaches or rises above –3.75 mA entering the upper 10% of the rich control mode. This detection range change-over is not effected as long as the presently set current detection range is already for the upper detection range.

If the determination at step 202 is NO, on the other hand, it is determined at step 204 whether the detected current value resides inside a lower limit range of the presently set current detection range. The lower limit range is set to be at about the lower 10% of the present current detection range, i.e., within an overlapping range of 20 to 25% between two adjacent current detection ranges of FIG. 3. With the determination of YES at step 204, the presently set current detection range is changed over to the lower one at step 205. For instance, at the time the presently detected current reaches or falls below –4 mA entering the 10% lower limit range in the stoichiometric control mode, the detection range is changed over to the lower current detection range of the adjacent control mode, i.e., rich control mode. In the same manner, the detection range is changed over from the range for the lean control mode to that for the stoichiometric control mode if the presently detected current reaches or falls below 3.75 mA entering the lower 10% range of the lean control mode. This detection range change-over is not effected as long as the presently set current detection range is already for the lower detection range.

In the event that the determination at step 204 is NO, the detection range used at step 201 is maintained. In the process of FIG. 5, no change-over is made as long as the presently set current detection range is in the lean control mode and in the rich control mode even when the presently detected output current enters the upper and lower 10% limit ranges, respectively.

Figure 6:
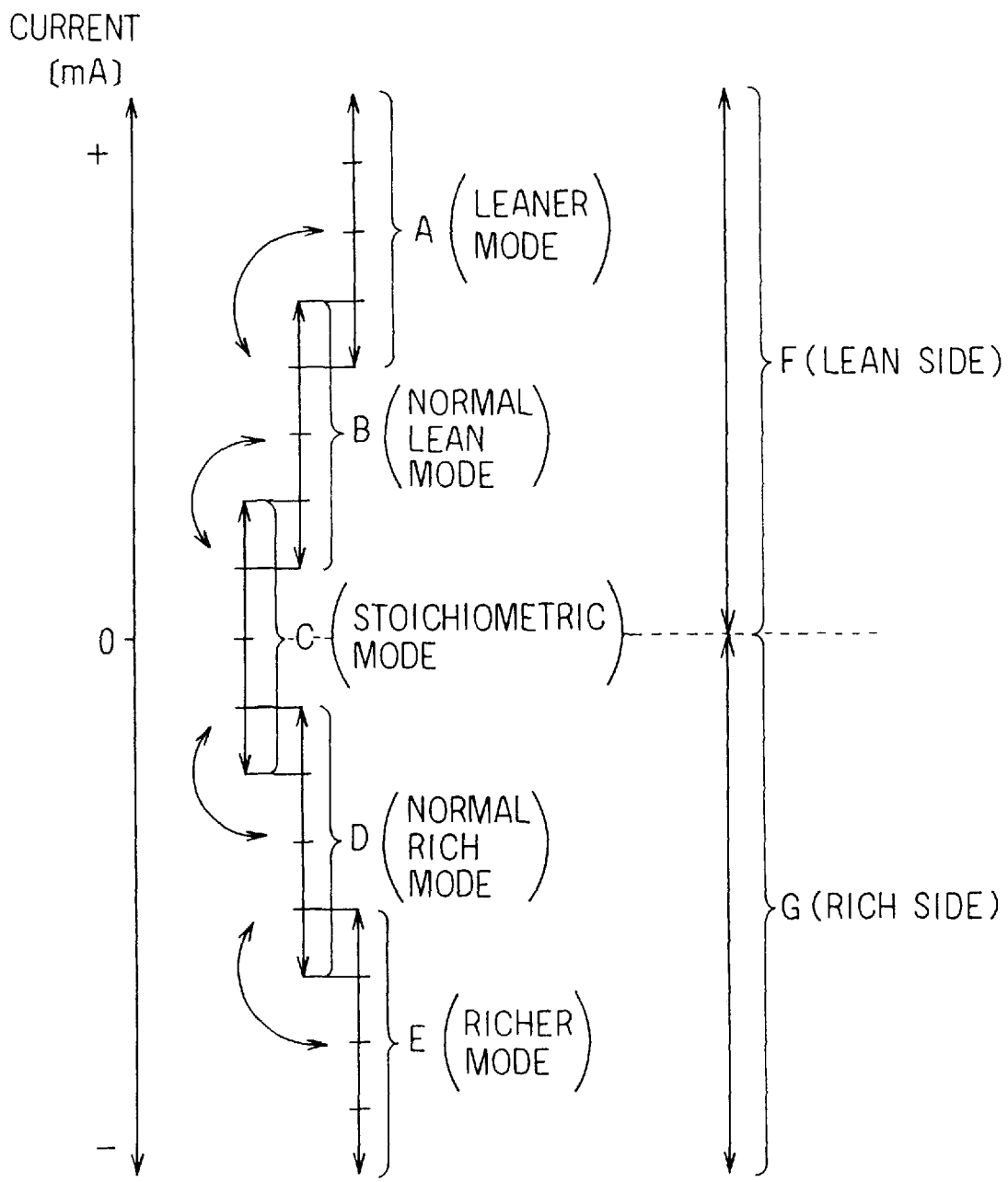
FIG. 6 is a chart illustrating current detection ranges in the case of five control modes or two control modes.

Although three current detection ranges are set for the lean, stoichiometric and rich control modes in the foregoing embodiment, the number of the ranges may be increased to five or reduced to two as shown in FIG. 6. In the case of setting five detection ranges, the current detection ranges may be set to correspond to such ranges for a leaner control mode (A), normal lean control mode (B), stoichiometric control mode (C), normal rich control mode (D) and richer control mode (E), respectively. According to this setting, even a very lean air-fuel ratio which will occur at the time of fuel cut-off operation due to engine deceleration can be detected in the current detection range for the leaner control mode (A). In the case of setting two detection ranges, the current detection ranges may be set to correspond to such ranges for a lean control mode (F) and rich control mode (G), respectively. In each case, the change-over between the adjacent two detection ranges may be made in the same manner as in the abovedescribed embodiment.

Figure 7:
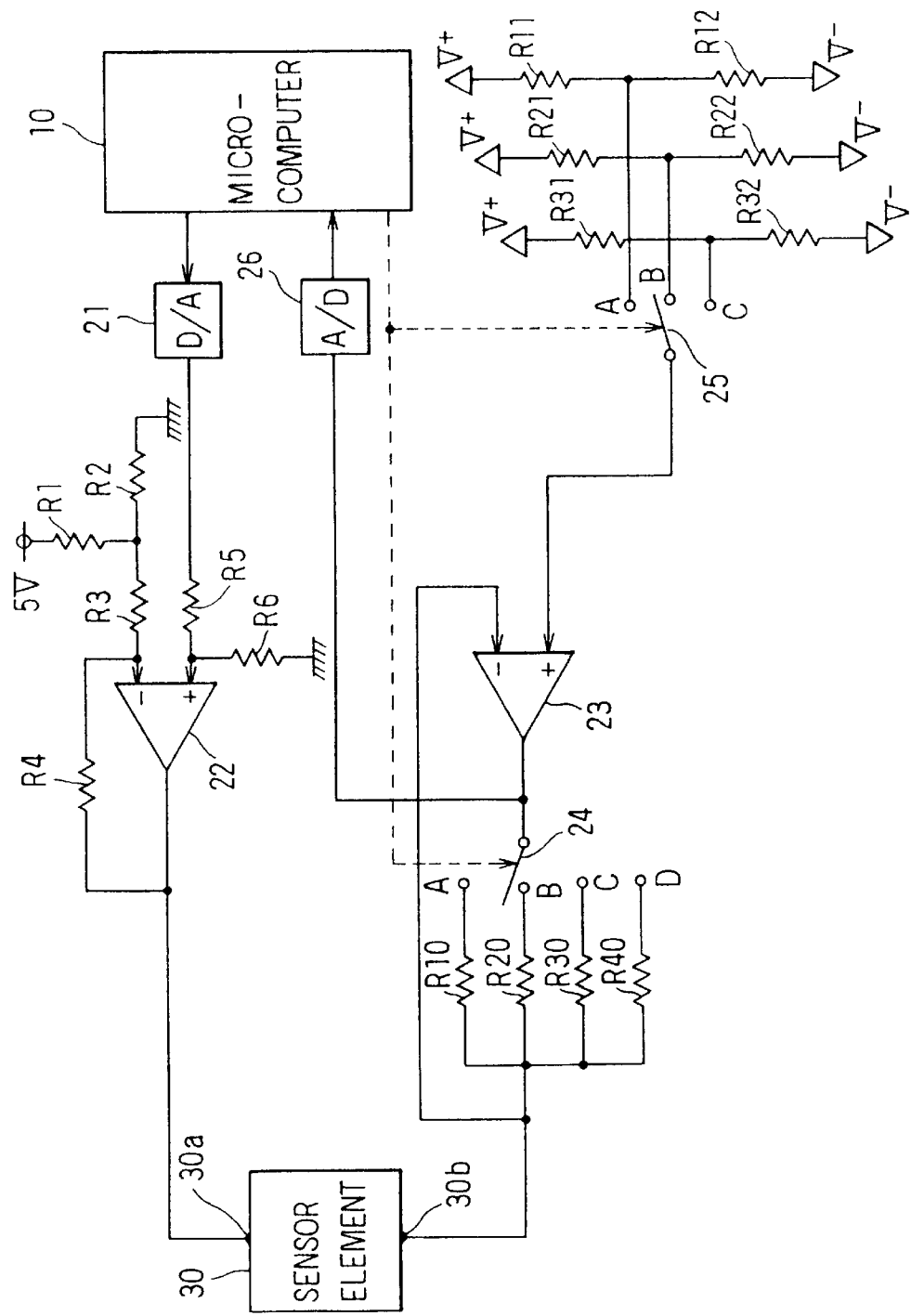
FIG. 7 is an electric wiring diagram illustrating a modification of the embodiment of FIG. 1.

Further, as illustrated in FIG. 7 as a modification of the embodiment of FIG. 1, another current detecting resistor R40 (50 Ω) may be connected to the sensor element 30 so that the change-over switch 24 may be connected thereto to detect the output currents in the range of 50 to −50 mA which corresponds to the range for the entire air-fuel ratios. In the case that the resistor R40 is used, the switch 25 should be connected to the terminal B. The resistor R40 is best used when the resistor R10 or R40 can not detect the output current accurately. Such a case includes an air-fuel ratio detection at the time of engine fuel cut-off operation or the like.

Still further, the current detection range may be switched over or shifted not by the actually detected current value but by the target air-fuel ratio.

It is to be understood that the present invention may be modified in many other ways without departing from the spirit and the scope of the invention.

What is claimed is:

1. An air-fuel ratio detecting apparatus comprising:
   a solid electrolyte sensor element disposed to produce an electric current corresponding to a gas concentration to be detected;
   a voltage supply disposed to apply a first voltage varying with a target gas-fuel ratio to a first terminal of said sensor element and a second voltage varying with a current detection range to a second terminal of said sensor element to thereby supply said sensor element with an operating voltage;
   a current detector disposed to detect an electric current produced by said sensor element; and
   a switch connected to switch said second voltage thereby to shift the current detection range of said current detector.

2. An air-fuel ratio detecting apparatus according to claim 1, wherein:
   said switch shifts said current detection range in response to at least one of:(a) said detected electric current, and (b) said target air-fuel ratio corresponding to said first voltage.

3. An air-fuel ratio detecting apparatus according to claim 1, wherein:
   said switch is arranged to shift said current detection range from one range presently used to another adjacent range when the detected current enters a predetermined limit range of said one range.

4. An air-fuel ratio detecting apparatus according to claim 1, wherein:
   said switch is arranged to shift said current detection range from one range presently used to another range: (a) first when a target air-fuel ratio is changed and (b) then when the detected current enters one of: (i) an upper limit range of said one range and (ii) a lower limit range of said one range.

5. An air-fuel ratio detecting apparatus according to claim 1, wherein:
   said current detector includes a plurality of resistors for current detection and switches connected to switch said resistors from one to another based on said current detection range.

6. An air-fuel ratio detecting apparatus according to claim 5, wherein:
   said resistors are divided into a first group adapted for current detection in a predetermined range and a second group adapted for current detection in a specified range within said predetermined range.

7. An air-fuel ratio detecting apparatus according to claim 5, wherein:
   said current detector includes resistors which are switched to reduce said electric current detecting range for a stoichiometric air fuel-ratio control mode as compared to other air-fuel ratio control modes.

8. An air-fuel ratio detecting apparatus according to claim 1, wherein:
   said switch includes voltage divider resistors for variably dividing a predetermined supply voltage to provide said second voltage.

9. An air-fuel ratio detecting apparatus according to claim 1, wherein:
   the voltage supply varies said first voltage in accordance with switching between feedback control to a stoichiometric air-fuel ratio mode and a lean air-fuel ratio mode; and
   said switch varies said second voltage in response to switching between said feedback control modes.

10. An air-fuel ratio detecting apparatus according to claim 9, wherein:
    said switch includes voltage divider resistors variably dividing a predetermined supply voltage to provide said second voltage; and
    said second voltage is switched to be higher for said stoichiometric air-fuel ratio feedback control mode than for said lean air-fuel ratio feedback control mode.

11. An air-fuel ratio detector having selectable different width measurement ranges which nevertheless have comparable detection accuracy, said detector comprising:
    a solid electrolyte gas sensor;
    a selectively variable operating supply voltage generator connected across said sensor and including selectable different ranges of operating voltage to be applied to the sensor;
    selectively variable resistance connected in circuit with said sensor to carry an electrical measured sensor current proportional to the current produced by said sensor; and
    a sensor controller connected to coordinate changes in said operating voltage and said resistance so as to maintain the accuracy of said measured sensor current as the range width of sensor operation is changed.

12. An air-fuel ratio detecting method comprising the steps of:
    supplying a solid electrolyte oxygen responsive sensor element with an operating voltage varying in accordance with a target air-fuel ratio to which a combustible mixture is feedback controlled, said sensor element producing an electric current corresponding to an oxygen concentration;
    converting said electric current from said sensor element to a detection voltage by a resistance; and
    determining an actual air-fuel ratio from said detection voltage; and
    switching to select different values of said operating voltage and said resistance when the target air-fuel ratio is switched from one in a first predetermined range to another in a second predetermined range, said switching requiring said detection voltage to vary within the same voltage range irrespective of the change in said target air-fuel ratio.

13. An air-fuel ratio detecting method comprising the steps of:

supplying a solid electrolyte oxygen responsive sensor element with an operating voltage varying in accordance with a target air-fuel ratio to which a combustible mixture is feedback controlled, said sensor element producing an electric current corresponding to an oxygen concentration;

converting said electric current from said sensor element to a detection voltage by a resistance;

determining an actual air-fuel ratio from said detection voltage; and switching to select different values of said operating voltage and said resistance when the detection voltage reaches a predetermined limit within a predetermined detection range, said switching requiring said detection voltage to vary within the same voltage range irrespective of a change from one predetermined range to another.

14. A method of detecting an air-fuel ratio over selectable different width measurement ranges which nevertheless have comparable detection accuracy, said method comprising:

selectively varying the operating supply voltage across a solid electrolyte gas sensor between selectable different ranges of operating voltage;

selectively varying a resistance connected in circuit with said sensor to carry an electrical measured sensor current proportional to electrical current produced by said sensor; and coordinating changes in said operating voltage and said resistance so as to maintain the accuracy of said measured sensor current as the range width of sensor operation is changed.

* * * * *